(12) United States Patent
Okamura

(10) Patent No.: US 10,238,835 B2
(45) Date of Patent: Mar. 26, 2019

(54) INTRODUCER SHEATH

(71) Applicant: TERUMO KABUSHIKI KAISHA, Shibuya-ku, Tokyo (JP)

(72) Inventor: Ryo Okamura, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/223,561

(22) Filed: Jul. 29, 2016

(65) Prior Publication Data
US 2016/0331930 A1 Nov. 17, 2016

Related U.S. Application Data

(63) Continuation of application No. 14/143,201, filed on Dec. 30, 2013, now Pat. No. 9,498,598, which is a
(Continued)

(30) Foreign Application Priority Data

Jul. 4, 2011 (JP) .................................. 2011-148578
Jul. 4, 2011 (JP) .................................. 2011-148581

(51) Int. Cl.
*A61M 25/00* (2006.01)
*A61M 25/06* (2006.01)
(Continued)

(52) U.S. Cl.
CPC ........ *A61M 25/0097* (2013.01); *A61M 25/01* (2013.01); *A61M 25/0662* (2013.01); *A61M 39/0606* (2013.01); A61M 2039/064 (2013.01)

(58) Field of Classification Search
CPC ........ A61M 2039/062; A61M 39/0693; A61M 39/0613
See application file for complete search history.

(56) References Cited

U.S. PATENT DOCUMENTS 4,436,519 A * 3/1984 O'Neill ................. A61M 39/04
137/847
4,610,665 A * 9/1986 Matsumoto ....... A61M 39/0606
604/167.04
(Continued)

FOREIGN PATENT DOCUMENTS

CN       1874808 A     12/2006
CN     101808691 A      8/2010
(Continued)

OTHER PUBLICATIONS

Decision of Refusal dated Aug. 15, 2016 by the Japanese Patent Office in corresponding Japanese Patent Application No. 2013-522871, and translation thereof (9 pages).
(Continued)

*Primary Examiner* — Scott Medway
(74) *Attorney, Agent, or Firm* — Buchanan Ingersoll & Rooney PC

(57) ABSTRACT

An introducer sheath is disclosed having a high centering performance that is relatively easily capable of introducing an elongated body such as a catheter into an appropriate position, and is capable of appropriately maintaining hemostasis and insertibility of a valve body. The introducer sheath includes a tubular member provided with a hollow section through which an elongated body is freely insertable, a hub that includes an inner space which communicates with the hollow section of the tubular member and is provided on a proximal side of the tubular member, a valve body that is placed in the inner space of the hub, and an annular member that contacts with the valve body to fix the valve body to the inner space and includes a through-hole into which the elongated body can be inserted.

18 Claims, 6 Drawing Sheets

Related U.S. Application Data continuation of application No. PCT/JP2012/066272, filed on Jun. 26, 2012.

(51) Int. Cl.
*A61M 39/06* (2006.01)
*A61M 25/01* (2006.01)

(56) References Cited

U.S. PATENT DOCUMENTS

| | | | | |
|---|---|---|---|---|
| 4,960,412 | A * | 10/1990 | Fink | A61M 39/0606 604/167.04 |
| 5,006,113 | A * | 4/1991 | Fischer | A61M 39/0606 604/167.04 |
| 5,092,857 | A * | 3/1992 | Fleischhacker | A61M 39/0606 137/846 |
| 5,167,637 | A * | 12/1992 | Okada | A61M 39/0606 251/149.1 |
| 5,178,607 | A * | 1/1993 | Lynn | A61B 5/15003 600/575 |
| 5,188,620 | A * | 2/1993 | Jepson | A61J 1/2089 604/415 |
| 5,199,948 | A * | 4/1993 | McPhee | A61M 39/045 604/167.02 |
| 6,258,065 | B1 * | 7/2001 | Dennis | A61B 17/3462 604/167.01 |
| 6,322,541 | B2 * | 11/2001 | West | A61M 39/0606 137/844 |
| 7,563,250 | B2 * | 7/2009 | Wenchell | A61B 17/3417 604/167.01 |
| 8,002,750 | B2 * | 8/2011 | Smith | A61B 17/3498 604/167.03 |
| 2001/0041872 | A1 * | 11/2001 | Paul, Jr. | A61M 39/0606 604/167.04 |
| 2002/0010425 | A1 * | 1/2002 | Guo | A61M 39/06 604/167.04 |
| 2003/0014015 | A1 * | 1/2003 | Tansey, Jr. | A61M 39/0606 604/167.04 |
| 2005/0192537 | A1 * | 9/2005 | Osborne | A61M 39/0606 604/167.01 |
| 2006/0069352 | A1 | 3/2006 | Eisenkolb et al. | |
| 2007/0028979 | A1 | 2/2007 | Yokota et al. | |
| 2010/0179480 | A1 * | 7/2010 | Sugiki | A61M 39/0606 604/167.04 |
| 2010/0185153 | A1 | 7/2010 | Sugiki et al. | |
| 2010/0268163 | A1 | 10/2010 | Rowe et al. | |
| 2013/0046241 | A1 | 2/2013 | Okamura et al. | |

FOREIGN PATENT DOCUMENTS

| | | |
|---|---|---|
| EP | 2 213 328 A1 | 8/2010 |
| JP | 59-133877 A | 8/1984 |
| JP | 64-31752 U | 2/1989 |
| JP | 08-131552 A | 5/1996 |
| JP | 2004-535258 A | 11/2004 |
| JP | 2009-142665 A | 7/2009 |
| WO | WO 98/13083 A1 | 4/1998 |
| WO | WO 99/06099 A2 | 2/1999 |
| WO | WO 2009/041522 A1 | 4/2009 |
| WO | WO 2011/115048 A1 | 9/2011 |

OTHER PUBLICATIONS

International Search Report (PCT/ISA/210) dated Oct. 9, 2012, by the Japanese Patent Office as the International Searching Authority for International Application No. PCT/JP2012/066272.
Chinese Office Action dated Mar. 26, 2015, by the Chinese Patent Office in corresponding Chinese Patent Application No. 201280031875.7 (8 pgs).
The extended European Search Report dated May 4, 2015, by the European Patent Office in corresponding European Patent Application No. 12808201.3-1506. (7 pgs).
Office Action dated Jan. 12, 2016, by the Japanese Patent Office in corresponding Japanese Patent Application No. 2013-522871. (8 pgs).
Office Action dated Jan. 20, 2016 by the European Patent Office in corresponding European Patent Application No. 12 808 201.3 (5 pages).

* cited by examiner

US 10,238,835 B2

INTRODUCER SHEATH

CROSS REFERENCES TO RELATED APPLICATIONS

This application is a continuation of U.S. patent application Ser. No. 14/143,201, filed on Dec. 30, 2013, which is a continuation of International Application No. PCT/JP2012/066272, filed on Jun. 26, 2012, and claims priority to Japanese Application No. 2011-148578, filed on Jul. 4, 2011 and Japanese Application No. 2011-148581, filed on Jul. 4, 2011, the entire content of each is incorporated herein by reference.

TECHNICAL FIELD

The present invention generally relates to an introducer sheath that is used to introduce a device into a body lumen.

BACKGROUND DISCUSSION

In recent years, various types of treatments and diagnoses have been performed in the medical field using an elongated and hollow tubular-shaped medical instrument called a catheter. Examples of such treatment methods include directly administering an agent into an affected area by using the elongatedness of the catheter, opening a narrowed section in the body lumen by using a catheter in which a balloon expanded by pressure is attached to a distal end thereof, scraping and opening the affected area by using a catheter in which a cutter is attached to a distal section of the catheter, and closing arterial aneurysm, bleeding, or feeding vessel sites with a filling material using the catheter. Other examples include embedding and placing a tubular-shaped stent which has a mesh-shaped side surface into the body lumen using the catheter so as to maintain an open state of the narrowed section in the body lumen, and suctioning excess liquid for a body in the body.

In general, in a case where the treatment, diagnosis, or the like is performed using the catheter, a introducer sheath is introduced into a puncture site formed in an arm or a leg and the catheter or the like is percutaneously inserted into a lesion area such as a blood vessel via a lumen of the introducer sheath.

Usually, a valve body that prevents blood reflux while allowing the device such as the catheter or a dilator to be inserted is disposed in a hub of the introducer sheath, which has a structure such that the device is inserted via the valve body from an opening section disposed on a proximal side of the hub. An example is disclosed in Japanese Application Publication No. 8-131552.

Also, in the introducer sheath according to U.S. Pat. No. 6,322,541, a deformable valve body in which a through-hole that has a slit is formed is bent so as to adjust hemostasis by and insertibility of the device.

However, in the introducer sheath disclosed in Japanese Application Publication No. 8-131552, the opening section into which the device such as the catheter is narrow, and an outer circumference of the opening section is formed to be a flat surface, and thus it is difficult to insert the device.

Also, in the introducer sheath according to U.S. Pat. No. 6,322,541, a hub surface and a cap surface sandwiching the valve body are bent, and thus the valve body is likely to be moved along the bending of the hub and the cap when the device is inserted. In addition, the introducer sheath according to U.S. Pat. No. 6,322,541 may be changed the hemostasis and the insertibility of the device by the degree of fusion of the cap.

SUMMARY

The introducer sheath disclosed here is relatively easily capable of introducing an elongated body such as a catheter into an appropriate position and has excellent centering performance The introducer sheath is also capable of appropriately maintaining hemostasis and insertibility of a valve body.

The introducer sheath according to one aspect includes a tubular member that includes a hollow section through which an elongated body is freely insertable, a hub that includes an inner space which communicates with the hollow section of the tubular member and is provided on a proximal side of the tubular member, a valve body that is placed in the inner space of the hub, and an annular member that contacts the valve body to fix the valve body to the inner space and includes a through-hole into which the elongated body can be inserted.

A wall surface of the through-hole decreases in diameter from the proximal side toward a distal side and is formed to be a curved surface in a direction from the proximal side toward the distal side.

At least one of the annular member and the hub includes a flat surface section that has a flat surface which contacts with the valve body, and a protrusion section that protrudes toward the valve body so that the center of the valve body is pressed to be concave toward the distal side.

In the introducer sheath disclosed here, since the wall surface of the through-hole decreases in diameter from the proximal side toward the distal side and is formed to be the curved surface in the direction from the proximal side toward the distal side, a distal end of the elongated body that is in contact with the wall surface can be easily and smoothly introduced toward the valve body by the wall surface which is formed to be the curved surface, and excellent centering performance can be achieved. The wall surface of the through-hole decreasing in diameter from the proximal side toward the distal side means the inner diameter of the wall surface of the through-hole decreasing from the proximal side toward the distal side.

In the annular member, the radial direction width of a projection plane that is the wall surface of the through-hole viewed from the proximal side is equal to or larger than the radial direction width of a position that is formed radially outside the wall surface of the through-hole on the projection plane. The distal end of the elongated body is likely to be in contact with the wall surface that is formed to be the curved surface, and the centering performance is improved.

When the entire surface facing the proximal side of the annular member is configured to be the curved surface, the distal end of the elongated body that is in contact with the wall surface can be smoothly introduced toward the valve body by the wall surface that is formed to be the curved surface, and the centering performance is improved.

When a curve on a cross section along the direction from the proximal side toward the distal side of the curved surface constituting the wall surface of the through-hole is a line drawn by one of a parabola, a quadratic function, an exponential function, or a logarithmic function, the angle of the curve can be changed to be larger from the proximal side toward the distal side of the curved surface, and resistance is reduced when the elongated body is inserted to be introduced into the distal side and the insertibility is improved.

The distal side angle of a distal side end section of the through-hole is larger than the proximal side angle of a proximal side end section of the through-hole as for the inclination angle of a tangent of the curve with respect to a surface that is orthogonal to the passing direction of the through-hole. The inclination angle is thus changed to be larger from the proximal side toward the distal side of the through-hole, and the resistance is reduced when the elongated body is inserted to be introduced into the distal side and the insertibility is improved.

The inclination angle of the curve continuously changes from the proximal side angle to the distal side angle, and so the elongated body that is in contact with the through-hole can be smoothly slid.

A proximal side slit is provided on a surface that is on the proximal side of the valve body and the distal side end section of the through-hole is positioned on a further central side of the valve body than end sections of the proximal side slit of the valve body. The elongated body that is in contact with the wall surface of the through-hole is introduced further into the central side of the valve body than the end section of the proximal side slit all the time, and so the elongated body is smoothly inserted into the slit of the valve body and the insertibility is improved, and damage to the valve body caused by the elongated body being in contact with a position apart from the slit of the valve body can be suppressed.

A distal side slit is provided on a surface of the valve body that is formed on the distal side, and the distal side end section of the through-hole is positioned at a position further on the central side of the valve body than end sections of the distal side slit of the valve body. The distal side slit is thus likely to receive force in the opening direction and the distal side slit is maintained in a further open state.

The curve on the cross section along the direction from the proximal side toward the distal side of the curved surface constituting the wall surface of the through-hole can have an inflection point, and so a convex surface and a concave surface are formed across the inflection point, and characteristics can be changed according to a wall surface area.

Since at least one of the annular member and the hub includes a flat surface section that has a flat surface which contacts with the valve body and a protrusion section that protrudes toward the valve body so that the center of the valve body is pressed to be concave toward the distal side, the valve body can be bent by the protrusion section to give appropriate hemostasis and insertibility, a movement of the valve body can be suppressed by the flat surface section, and the hemostasis and insertibility can be maintained in an appropriate state.

The annular member can include the protrusion section that protrudes toward the distal side in a distal side circumferential edge section of the through-hole. The valve body can thus be bent by the protrusion section and the hemostasis and insertibility can be improved.

When the valve body includes the distal side slit on the surface that is formed on the distal side and the distal side slit is opened by pressing by the protrusion section, sliding resistance during the insertion of the elongated body is reduced and the insertibility is improved.

The protrusion section can constitute a distal side terminal end of the wall curved surface. The distal of the elongated body that is introduced into the central side of the wall surface can thus be smoothly introduced into the valve body as it is.

According to another aspect, an introducer sheath into which an elongated medical device is insertable comprises: a sheath tube through which extends a lumen that receives the elongated medical device, the sheath tube possessing a proximal end; a hub fixed to the sheath tube and positioned at the proximal end of the sheath tube, with the hub possessing a through hole extending throughout the hub and communicating with the lumen in the sheath tube, and with the hub possessing a recessed proximal end; a valve body positioned in the recessed proximal end of the hub and covering the through-hole in the hub in a liquid-tight manner; and an annular member separate from the valve body. The valve body possesses a proximal-facing surface facing away from the sheath tube and a distal-facing surface facing toward the sheath tube, and the valve body includes a slit that communicates with the distal-facing surface of the valve body. The annular member is mounted on the proximal end of the hub and is in contact with the distal-facing surface of the valve body, wherein the annular member possesses a through-hole passing completely through the annular member. The slit in the valve body is exposed at the through-hole in the annular member to permit the elongated medical device to be inserted through the through-hole in the annular member and into the slit in the valve body.

An introducer sheath is disclosed into which an elongated medical device is insertable, the introducer sheath comprising: a sheath tube through which extends a lumen that receives the elongated medical device, the sheath tube possessing a proximal end; a hub fixed to the sheath tube and positioned at the proximal end of the sheath tube, the hub possessing a through-hole extending throughout the hub and communicating with the lumen in the sheath tube, the hub possessing a recessed proximal end; a valve body positioned in the recessed proximal end of the hub and covering the through-hole in the hub in a liquid-tight manner, the valve body possessing a proximal-facing surface facing away from the sheath tube and a distal-facing surface facing toward the sheath tube, the valve body including a slit that communicates with the distal-facing surface of the valve body; and an annular member separate from the valve body, the annular member being mounted on the proximal end of the hub and in contact with the proximal-facing surface of the valve body, the annular member possessing a through-hole passing completely through the annular member, the slit in the valve body being exposed at the through-hole in the annular member to permit the elongated medical device to be inserted through the through-hole in the annular member and into the slit in the valve body, and wherein the annular member includes a protrusion section that protrudes toward the valve body so that a center of the valve body is pressed in a manner causing the valve body to be concave toward a distal side, the protrusion section contacting the valve body at a position further toward a central side of the valve body than end sections of a proximal side slit of the valve body, and the protrusion section having a curved proximal-facing surface.

An introducer sheath is disclosed comprising: a tubular member that includes a hollow section through which an elongated body is freely insertable; a hub that includes an inner space which communicates with the hollow section of the tubular member and is provided on a proximal side of the tubular member; a valve body positioned in the inner space of the hub, the valve body possessing a proximal-facing surface facing away from the tubular member and a distal-facing surface facing toward the tubular member, the valve body including a slit that communicates with the distal-facing surface of the valve body; and an annular member that contacts the valve body to fix the valve body in the inner space, the annular member including a through-hole into which the elongated body is insertable, the annular member possessing a through-hole passing completely through the annular member, the slit in the valve body being exposed at the through-hole in the annular member to permit the elongated medical device to be inserted through the through-hole in the annular member and into the slit in the valve body; and wherein the annular member includes a protrusion section that protrudes toward the valve body so that a center of the valve body is pressed in a manner causing the valve body to be concave toward the distal side, the protrusion section contacting the valve body at a position further toward a central side of the valve body than end sections of a proximal side slit of the valve body, and the protrusion section having a curved proximal-facing surface.

DETAILED DESCRIPTION

Figure 1:
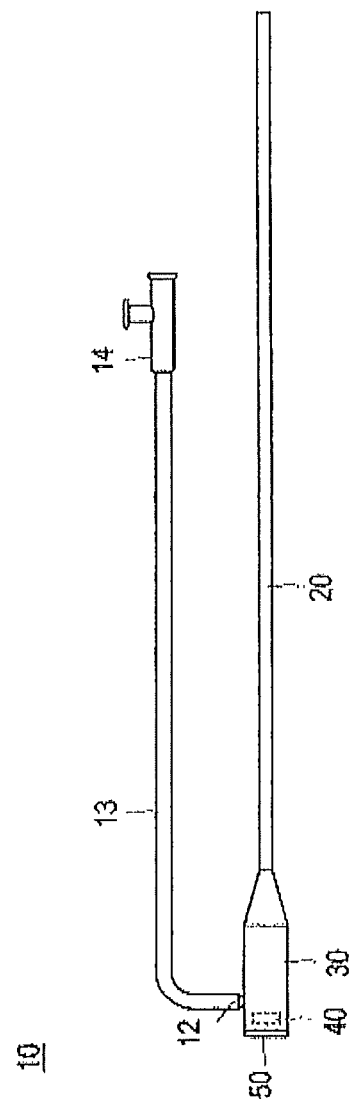
FIG. 1 is a plan view of an introducer sheath according to one embodiment disclosed here as an example of the disclosed introducer sheath.

An embodiment of the introducer sheath representing an example of the introducer sheath disclosed here is set forth below with reference to the accompanying drawings. Common features are identified by the same reference numerals throughout and so a detailed description of already described features is not repeated. In some cases, dimensional ratios in the drawings are exaggerated and are different from the actual ratios for the convenience of description.

A sheath 10 for introducer according to the embodiment is an instrument that ensures an access route into a body lumen and remains in the body lumen so that a medical device 100 (elongated body) (refer to FIG. 6), examples of which include a catheter, a guide wire, and an embolus material, is inserted into the sheath 10 for introducer and introduced into the body lumen. In the description which follows, the hand operation unit side of the sheath 10 for an introducer will be referred to as the "proximal side," and the side that is inserted into the body lumen will be referred to as the "distal side."

Figure 2:
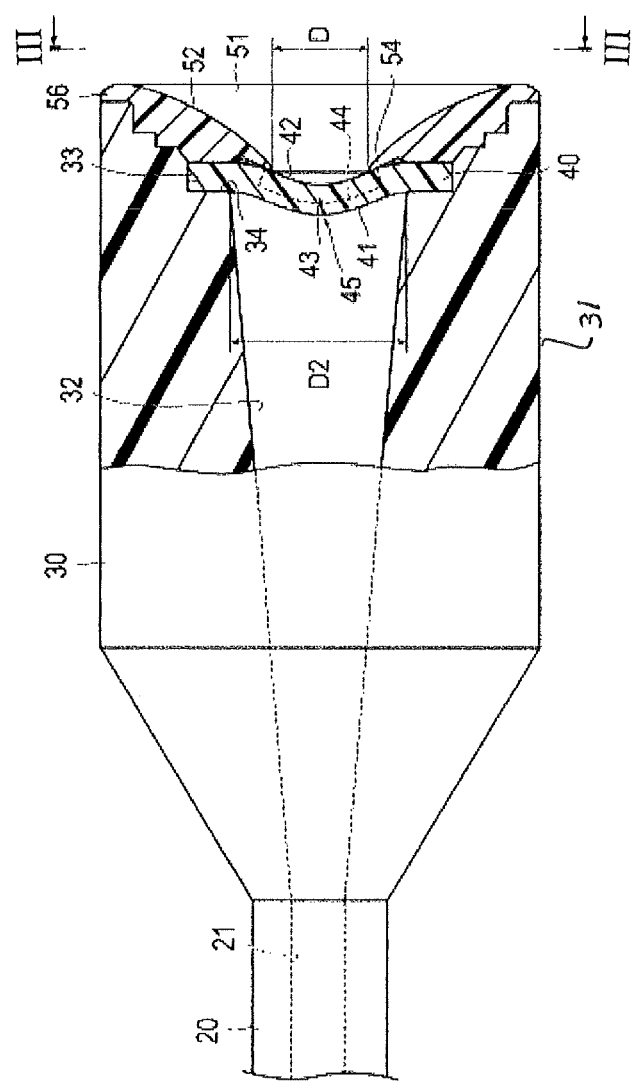
FIG. 2 is a partial cross-sectional view showing a proximal section of the introducer sheath.
Figure 3:
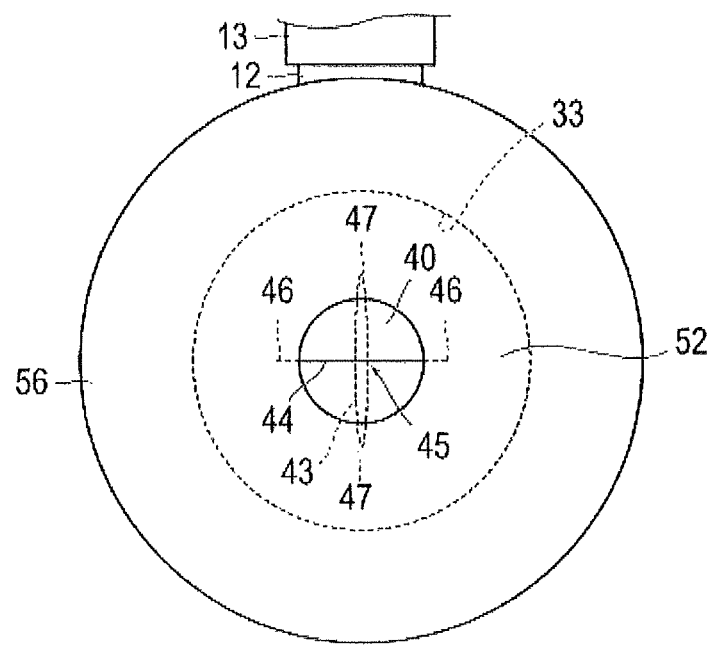
FIG. 3 is an arrow view taken along the section line III-III of FIG. 2.

Referring to FIGS. 1 to 3, the sheath 10 for introducer includes a sheath tube 20, a hub 30 that is attached to the proximal side of the sheath tube 20, a valve body 40 disposed in the hub 30, and an annular member 50 that fixes the valve body 40 to the hub 30.

The sheath tube 20 is a tubular member that has a hollow section 21 into which the device 100 such as the catheter can be inserted, and is percutaneously introduced into the body lumen. That is, the sheath tube or tubular member is hollow or includes a lumen extending throughout its longitudinal extent, and the lumen is open at its distal end to outside the sheath tube and communicates at its proximal end to a lumen in the hub 30.

Examples of a material constituting the sheath tube 20 include a polymer material such as polyolefin (for example, polyethylene, polypropylene, polybutene, an ethylene-propylene copolymer, an ethylene-vinyl acetate copolymer, an ionomer, and a mixture of at least two thereof), a polyolefin elastomer, a cross-linked body of polyolefin, polyvinyl chloride, polyamide, a polyamide elastomer, polyester, a polyester elastomer, polyurethane, a polyurethane elastomer, fluorine resin, polycarbonate, polystyrene, polyacetal, polyimide, and polyetherimide, and a mixture thereof.

A side port 12 that communicates with an inner section or interior of the sheath tube 20 is formed in the hub 30. One end of a tube 13 that is formed of, for example, polyvinyl chloride and has flexibility is liquid-tightly connected to the side port 12. A three-way stopcock 14, for example, is mounted on the other end of the tube 13. A liquid, an example of which includes physiological saline, is injected via the tube 13 into the sheath 10 for an introducer from a port of the three-way stopcock 14.

Referring to FIG. 2, the hub 30 has a hub main body 31, a central through hole 32 (inner space) that communicates with the hollow section 21 of the sheath tube 20 and which is formed in the hub main body 31, and an accommodation section 33 (inner space) that is disposed on the proximal side of the central hole 32 and accommodates the valve body 40. The inner diameter of the accommodation section 33 is larger than the inner diameter of the central hole 32. The accommodation section 33 has a support surface 34 with which an end surface of the valve body 40 contacts. In the illustrated embodiment, the accommodation section is a recessed portion of the hub that is recessed in the distal direction relative to the proximal-most end surface of the hub 30.

A material constituting the hub 30 is not particularly limited, but a hard material such as hard resin is suitable. Specific examples of the hard resin include polyolefin such as polyethylene and polypropylene, polyamide, polycarbonate, and polystyrene.

Figure 4:
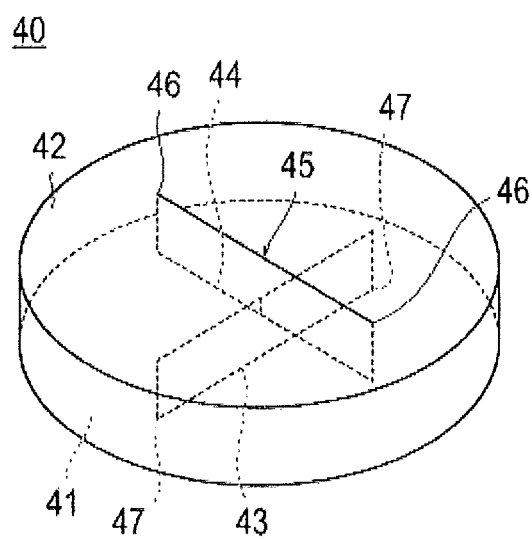
FIG. 4 is a perspective view showing a valve body.

Referring to FIGS. 2 to 4, the valve body 40 is formed from a circular membrane-shaped (disk-shaped) elastic member, and is liquid-tightly fixed to the hub 30 to span or cover the hole 32 in the hub. The valve body 40 includes the distal side surface which is referred to as a distal surface 41 and the end surface on the opposite side which is referred to as a proximal surface 42.

A distal side slit 43 that reaches or intersects with (opens to) only the distal surface 41 is formed on the distal surface 41 of the valve body 40. A proximal side slit 44 that reaches or intersects with (opens to) only the proximal surface 42 is formed on the proximal surface 42 of the valve body 40. The insertion section 45 is formed in the valve body 40 in such a manner that the distal side slit 43 and the proximal side slit 44 cross each other in a cross shape and portions of the slits communicate with each other in a central section where the slits overlap each other.

A material constituting the valve body 40 is not particularly limited, but examples of the material include an elastic member such as silicone rubber, latex rubber, butyl rubber, and isoprene rubber.

Figure 5:
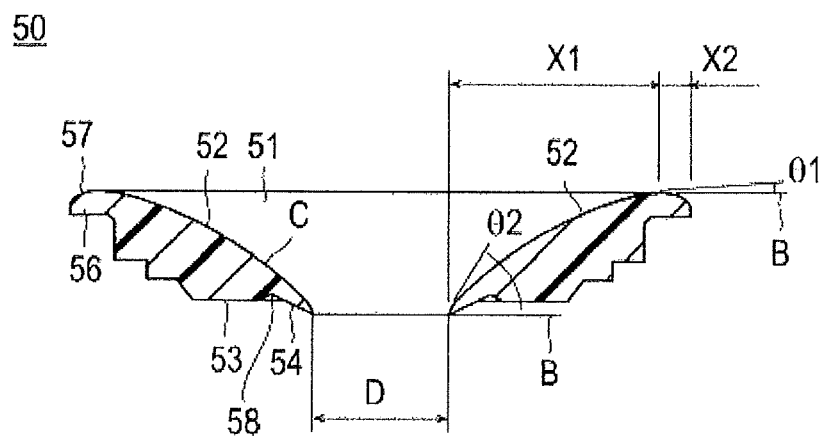
FIG. 5 is a cross-sectional view showing a sealing member.

Referring to FIGS. 2, 3, 5, and 8, the annular member 50 has a through-hole 51 that passes through from the proximal side to the distal side, and a wall surface 52 constituting the through-hole 51 decreasing in diameter from the proximal side toward the distal side and is formed to be a convex curved surface in a direction from the proximal side toward the distal side. In other words, the wall surface 52 is a convex curve so that the inner diameter of the through-hole 51 is decreased on a cross section along the direction from the proximal side toward the distal side. As shown in FIG. 5, in the annular member 50, the radial direction width X1 of a projection plane that is the wall surface 52 of the through-hole 51 viewed from the proximal side is equal to or larger than the radial direction width X2 of a proximal outer circumferential section 57 that is formed radially outward from the wall surface 52 of the through-hole 51 on the projection plane. The point at which the wall surface 52 ends and the outer circumferential section begins is the point at which the wall surface 52 no longer curves inwardly and in the distal direction. More specifically, this point is radially inward from the outer circumference of the hub 30 and is formed at the portion where the wall surface 52 begins to curve inwardly and in the distal direction. The entire surface facing the proximal side of the annular member 50, that is, the entire surface formed from the wall surface 52 and the proximal outer circumferential section 57 is configured to be a curved surface.

Also, the cross-section along the direction from the proximal side toward the distal side of the curved surface which constitutes the wall surface 52 of the through-hole 51 is a curve swelling toward the proximal side. In addition, the curve C is a parabola. The curve C is not limited to the parabola, and for example, may be a line drawn by a quadratic function, an exponential function, or a logarithmic function.

As for the inclination angle of a tangent of the curve C with respect to a surface B that is orthogonal to the passing direction (central axis) of the through-hole 51, the distal side angle θ2 of a distal side end section of the through-hole 51 is larger than the proximal side angle θ1 of a proximal side end section of the through-hole 51, and the formula (1) described below is satisfied. The θ1 is zero degree in the embodiments.

$$90 \text{ degrees} \geq \theta2 \geq \theta1 \geq \text{zero degree} \quad \text{Formula (1)}$$

The inclination angle of the curve C continuously changes from the proximal side angle θ1 to the distal side angle θ2.

The annular member 50 is shaped or configured to be fitted into the hub 30, and a flange section 56 laterally extending from an outer circumferential section of the annular member 50 is thermally welded or bonded with the hub 30, and the valve body 40 is pinched between the hub 30 and the flange section 56. An annular flat surface section 53 that is formed from a flat surface contacting the valve body 40, and a protrusion section 54 that is annularly formed on a radially inner side of the flat surface section 53 and protrudes toward the valve body 40, are formed on the distal side of the annular member 50. The protrusion section 54 protrudes from a distal side circumferential edge section of the through-hole 51 toward the valve body 40, and constitutes a distal side terminal end of the wall surface 52. The protrusion section 54 protrudes from the distal side circumferential edge section of the through-hole 51 toward the central section (central axis) of the through-hole 51 and protrudes in the distal side direction. A distal side section 54a of the protrusion section 54 has a linear shape on a cross-section, and contacts the valve body 40 in a planar shape or planar portion. The length of the protrusion section 54 toward the central section of the protrusion section 54 is longer than the length of the protrusion section 54 toward the distal side direction. The thickness of the protrusion section 54 decreases toward the central section.

The inner diameter D of a distal side terminal end of the protrusion section 54 of the annular member 50 is smaller than the inner diameter D2 of the side of the annular member in contact with the valve body 40 of the hub 30. The protrusion section 54 reaches a further inner side than the inner diameter D2 of the hub 30. That is, the inner periphery of the protrusion section 54 extends further radially inwardly than the inner surface of the central hole 32 at the diameter D2.

The protrusion section 54 presses the proximal surface 42 of the valve body 40 to elastically deform the valve body 40, and causes the center of the valve body 40 to be recessed so that the center of the valve body is concave toward the distal side. In this manner, the proximal side slit 44 is in a state of receiving force in a blocking direction, and the distal side slit 43 is in a state of receiving force in an opening direction.

The protrusion section 54 contacts a position further on the central side of the valve body 40 than the end sections 46 of the proximal side slit 44 of the valve body 40 for the pressing. Also, the protrusion section 54 contacts and presses the valve body 40 at a position further on the central side of the valve body 40 than an end section 47 of the distal side slit 43 of the valve body 40.

The flat surface section 53 of the annular member 50 is disposed substantially parallel to the support surface 34 of the hub 30. The flat surface section 53 elastically deforms the valve body 40 in the distal side direction between the support surface 34 and the flat surface section 53 to fix the valve body.

Figure 8:
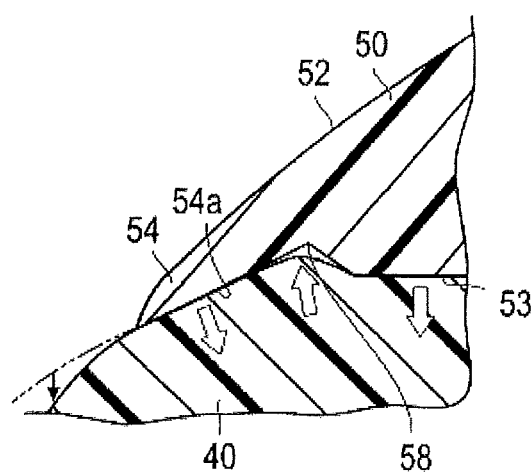
FIG. 8 is a partial cross-sectional view showing a deformation of the valve body at the time when the elongated body is inserted into the introducer sheath.

Also, an annular concave section 58 that is recessed toward the proximal side or in the proximal direction is formed on the central side of the flat surface section 53 of the annular member 50 (refer to FIGS. 5 and 8).

It is preferable that the distal side inner diameter D of the through-hole 51 be slightly larger than the outer diameter of the device 100 such as the catheter which is inserted into the through-hole so as to increase centering performance. As an example, in a case where the device 100 is a 6Fr guiding catheter, the distal side inner diameter D2 of the through-hole 51 can be approximately 2.20 mm with respect to the outer diameter of 2.17 mm of the guiding catheter. Also, as the distal side inner diameter D of the through-hole 51 is slightly larger than the outer diameter of the device 100, the device 100 can be in contact with an edge section of the inner diameter D so that the device 100 can be operated and operability is improved.

A material constituting the annular member 50 is not particularly limited, but a hard material such as hard resin is suitable. Specific examples of the hard resin include polyolefin such as polyethylene and polypropylene, polyamide, polycarbonate, and polystyrene.

Next, an insertion operation of the device 100 such as the catheter using the sheath 10 for introducer will be briefly described below.

First, a predetermined position on the skin is perforated or punctured by using an introducer needle or the like, and the guide wire is inserted into, for example, a blood vessel through the perforation or puncture. The guide wire is inserted from a distal end of the sheath 10 for introducer into a lumen in the sheath, and the sheath 10 for introducer is inserted into the blood vessel along the guide wire. When the sheath 10 for introducer is inserted, it is preferable that a dilator that assists in the insertion is combined on an inner side of the sheath 10 for introducer. After the sheath 10 for introducer is inserted into the blood vessel, the dilator and the guide wire are removed so that only the sheath 10 for introducer remains. In this manner, the sheath 10 for introducer functions as a passage that connects an outer side of the body and an inner side of the blood vessel, and the device 100 such as the catheter can be inserted into the blood vessel through the sheath.

Next, an effect of the sheath 10 for introducer according to the embodiment will be described.

Figure 6:
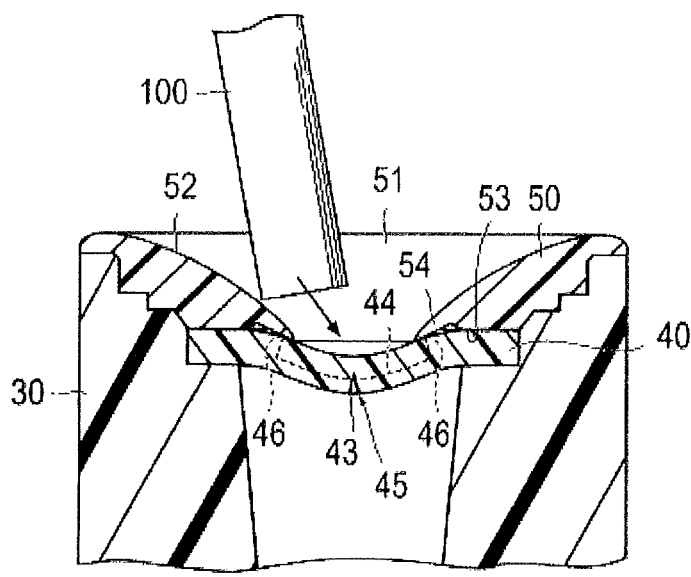
FIG. 6 is a partial cross-sectional view of the proximal section at a time when an elongated body is inserted into the introducer sheath.

In the sheath 10 for introducer according to the embodiment, the wall surface 52 that is formed in the through-hole 51 decreases in diameter from the proximal side toward the distal side, and is formed to be the convex curved surface in the direction from the proximal side toward the distal side. Accordingly, as shown in FIG. 6, a distal end of the device 100 that is in contact with the wall surface 52 can be smoothly introduced toward the valve body 40 by the wall surface 52 which is the curved surface when the device 100 such as the catheter is inserted into the through-hole 51 of the annular member 50. Also, since the wall surface 52 of the through-hole 51 is the curved surface in the direction from the proximal side toward the distal side, the inclination angle with respect to the central axis decreases toward the central section, and thus resistance toward an insertion direction is decreased and insertibility is improved.

As shown in FIG. 5, since the radial direction width X1 of the projection plane that is the wall surface 52 of the through-hole 51 viewed from the proximal side is equal to or larger than the radial direction width X2 of the proximal outer circumferential section 57 on the projection plane, the distal end of the device 100 is likely to be in contact with the wall surface 52 formed as the curved surface and the centering performance is improved.

Also, since the entire surface facing the proximal side of the annular member 50 is configured to be a curved surface, the distal end of the device 100 that is in contact with the wall surface 51 can be smoothly introduced toward the valve body 40 by the wall surface 51 which is configured as the curved surface and the centering performance is improved.

Also, since the cross-section along the direction from the proximal side toward the distal side of the curved surface which constitutes the wall surface 52 is a curve swelling to the proximal side, the device 100 can be centered smoothly. In addition, since the curve C is a parabola, the angle of the curve C can be changed to be larger from the proximal side toward the distal side, and resistance is reduced when the device 100 is inserted to be introduced into the distal side and the insertibility is improved.

Also, since the distal side angle θ2 of the distal side end section of the through-hole 51 is larger than the proximal side angle θ1 of the proximal side end section of the through-hole 51, the resistance is reduced when the device 100 is inserted to be introduced into the distal side and the insertibility is improved.

Since the inclination angle of the curve C continuously changes from the proximal side angle θ1 to the distal side angle θ2, the device 100 that is in contact with the through-hole 51 can be smoothly slid.

Figure 7:
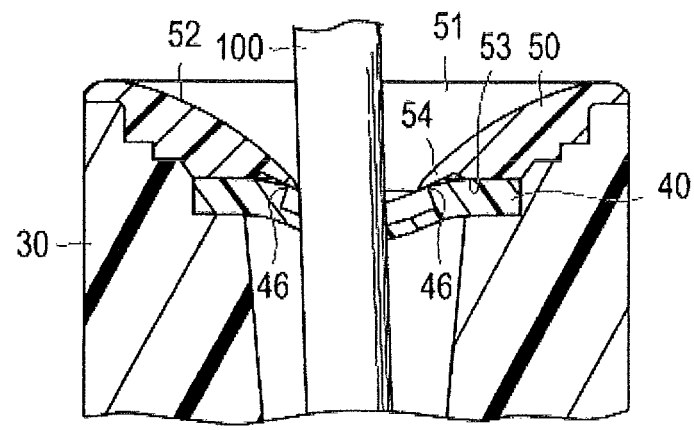
FIG. 7 is a partial cross-sectional view of the proximal section at the time when the elongated body is inserted into the introducer sheath.

Since the protrusion section 54 contacts the valve body at a position further toward the central side of the valve body 40 than the end sections 46 of the proximal side slit 44 of the valve body 40, the device 100 that is in contact with the wall surface 52 of the through-hole 51 is introduced further toward the central side of the valve body 40 than the end sections 46 of the proximal side slit 44 all the time, and the device 100 is smoothly inserted into the insertion section 45 of the valve body 40 and the insertibility is improved as shown in FIG. 7. Also, since the device 100 that is in contact with the wall surface 52 is introduced into the central side of the valve body 40, damage to the valve body 40 caused by the device 100 being in contact with a position spaced from the insertion section 45 of the valve body 40 can be suppressed.

Since the protrusion section 54 contacts the valve body at a position further toward the central side of the valve body 40 than the end section 47 of the distal side slit 43 of the valve body 40 for the pressing, the distal side slit 43 is likely to receive the force in the opening direction and the distal side slit 43 is maintained in a further open state.

Since the protrusion section 54 is formed to protrude from the distal side circumferential edge section of the through-hole 51 toward the central section of the through-hole 51 and the distal side direction, the recess of the valve body 40 and the curved surface of the wall surface 52 of the annular member 50 are continuously configured and the centering performance of the device is increased. Since the distal side section 54a of the protrusion section 54 has a linear shape on the cross section, and is in contact with the valve body 40 in a planar shape, a holding force with respect to the valve body 40 is improved. Since the length of the direction toward the central section of the protrusion section 54 is longer than the length toward the distal side direction, a gentle recess can be formed in the valve body 40. Since the long axis direction thickness of the protrusion section 54 decreases according to the direction toward the central section, the valve body 40 can be elastically pressed.

Also, since the inner diameter D of the distal side terminal end of the protrusion section 54 is smaller than the inner diameter D2 of the side in contact with the valve body 40 of the hub 30, the protrusion section 54 reaches the further inner side than the inner diameter D2 of the hub 30 and the centering performance is improved.

Since the protrusion section 54 protrudes from the distal side circumferential edge section of the through-hole 51 of the annular member 50 toward the valve body 40, the valve body 40 is pressed from the annular member 50 side (proximal side) and the valve body 40 can be rather easily bent (concave) toward the distal side by the protrusion section 54. Since the valve body 40 is pressed by the protrusion section 54 and the proximal side slit 44 receives the force in the blocking direction and the distal side slit 43 receives the force in the opening direction, a hemostasis effect is improved by the proximal side slit 44 that receives the force in the blocking direction and sliding resistance during the insertion of the device 100 is reduced by the distal side slit 43 in the open state and the insertibility is improved compared to a case where the valve body 40 is not concave but flat.

Also, since the proximal surface 42 of the valve body 40 is bent or curved into a concave shape by the protrusion section 54, the distal end of the device 100 can be guided by the concave-shaped proximal surface 42 of the valve body 40 itself and can be introduced into the central section where the resistance during the insertion is relatively small. Accordingly, the device 100 can be inserted with less force and the insertibility is improved.

Also, since the flat surface section 53 that contacts the valve body 40 along with the protrusion section 54 is formed in the annular member 50, a movement of the valve body 40 can be reliably suppressed by the flat surface section 53 and hemostasis and the insertibility can be maintained in an appropriate state. When the protrusion section 54 is not formed in the annular member 50 but the valve body 40 is pressed only with a flat surface, the amount of compression of the valve body 40 is not fixed but an individual difference increases, and centering and the insertibility of the device 100 are not uniform. However, in the embodiment, the valve body 40 is configured to be pressed by the protrusion section 54, and thus a desired amount of compression of the valve body 40 can be easily ensured, and the centering and insertibility of the device 100 can be relatively high all the time while almost no individual difference is generated. The flat surface section 53 is disposed substantially in parallel with the support surface 34 of the hub 30 and the flat surface section 53 fixes the valve body by elastically deforming the valve body 40 in the distal side direction between the support surface 34 and itself, and thus the movement of the valve body 40 can be reliably suppressed and the hemostasis and insertibility can be maintained in an appropriate state.

Also, since the annular concave section 58 that is recessed toward the proximal side (proximal direction) is formed on the central side of the flat surface section 53 of the annular member 50, a portion of the valve body 40 escapes while receiving a force in the upper left direction (white arrow) shown in FIG. 8 in the annular concave section 58 (i.e., a portion of the valve body 40 deformed by elastic force and is inserted in or enters the annular concave section 58 of the annular member 50), and a force counteracting the force is applied to the valve central section in a state where the valve body 40 is pressed by the distal side section 54a of the protrusion section (refer to the lower right direction white arrow in FIG. 8) while the valve body 40 is pressed to the distal side (distal direction) by the flat surface section 53 (refer to the white down arrow in FIG. 8) as shown in FIG. 8. Accordingly, the valve body 40 that is deformed by the insertion of the device 100 (refer to the two-dot chain line in FIG. 8) can escape (i.e., is inserted in or enters the annular concave section 58) in the state where the valve body 40 is pressed simply by the protrusion section 54. Accordingly, the recess in the central section of the valve body 40 becomes larger and the centering performance is improved.

Since the protrusion section 54 constitutes the distal side terminal end of the wall surface 52, the distal of the device 100 that is introduced into the central side of the wall surface 52 can be smoothly introduced into the valve body 40 as it is as shown in FIG. 7.

Figure 9:
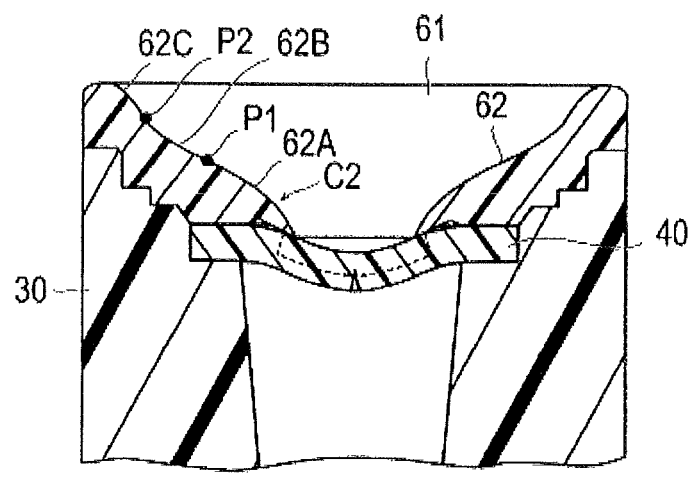
FIG. 9 is a partial cross-sectional view of a proximal section showing another example of the introducer sheath.

The present invention is not limited to the above-described embodiment as various modifications are possible within the scope of the claims. For example, as in another example of the introducer sheath shown in FIG. 9, a curve C2 on a cross-section along a direction from the proximal side to the distal side of a curved surface that constitutes a wall surface 62 of a through-hole 61 may have inflection points P1 and P2. In other words, a convex curved surface 62A is formed on the distal side (central side) of the wall surface 62, a concave curved surface 62B is formed on the proximal side (radially outer side) across the inflection point P1, and a convex curved surface 62C is formed further on the proximal side (radially outer side) across the inflection point P2. According to this configuration, the centering of the device 100 is performed while the distal end of the device 100 that is inserted into the through-hole 61 is prevented from deviating radially outward from the through-hole 61 on the concave curved surface 62B and the convex curved surface 62C, and the device 100 that is introduced from the curved surface 62B can be smoothly introduced into the valve body 40 on the convex curved surface 62A. The number of inflection points may be one or may be three or more. A curve of cubic or higher function, for example, can be used as the curve which has the inflection point.

Figure 10:
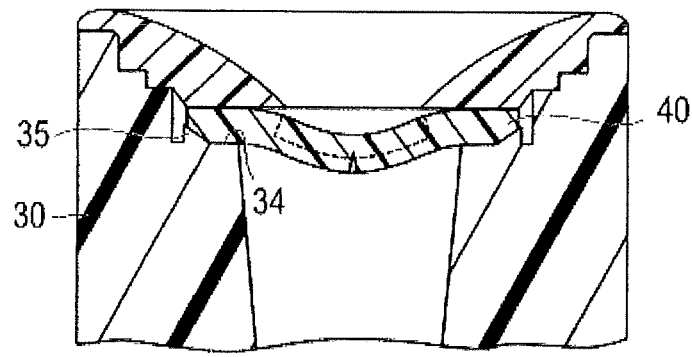
FIG. 10 is a partial cross-sectional view of a proximal section showing another example of the introducer sheath.

Also, the configuration in which the protrusion section 54 constitutes the distal side terminal end of the wall surface 52 of the through-hole 51 formed in the annular member 50 has been shown. However, the position at which the protrusion section is disposed and the structure of the protrusion section are not limited in this regard, and modifications are possible if the hemostasis and insertibility can be improved by bending the valve body 40 by the protrusion section. For example, the protrusion section may be disposed at another position of the annular member 50 and, as in another example of the introducer sheath shown in FIG. 10, an annular protrusion section 35 that protrudes toward the proximal side may be formed in an outer circumferential section of the support surface 34 of the hub 30 instead of the annular member side and the central section of the valve body 40 may be configured to be compressed to be concave toward the distal side.

Also, the through-hole of the annular member may not be the convex curved surface but can be a concave curved surface, a combination of a convex curved surface and a concave curved surface, a tapered shape with a linear cross section, or a hole with a constant inner diameter.

Also, the structure of the valve body need not be configured to have crossing slits.

The detailed description above describes an introducer sheath. The introducer sheath is disclosed by way of example. The invention is not limited, however, to the precise embodiment and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An introducer sheath into which an elongated medical device is insertable, the introducer sheath comprising:
   a sheath tube through which extends a lumen that receives the elongated medical device, the sheath tube possessing a proximal end;
   a hub fixed to the sheath tube and positioned at the proximal end of the sheath tube, the hub possessing a through-hole extending throughout the hub and communicating with the lumen in the sheath tube, the hub possessing a recessed proximal end;
   a valve body positioned in the recessed proximal end of the hub and covering the through-hole in the hub in a liquid-tight manner, the valve body possessing a proximal-facing surface facing away from the sheath tube and a distal-facing surface facing toward the sheath tube, the valve body including a slit that communicates with the distal-facing surface of the valve body;
   an annular member separate from the valve body, the annular member being mounted on the proximal end of the hub and in contact with the proximal-facing surface of the valve body, the annular member possessing a through-hole passing completely through the annular member, the slit in the valve body being exposed at the through-hole in the annular member to permit the elongated medical device to be inserted through the through-hole in the annular member and into the slit in the valve body;

the annular member including a protrusion section that protrudes toward the valve body so that a center of the valve body is pressed in a manner causing the valve body to be concave toward a distal side, the protrusion section contacting the valve body at a position further toward a central side of the valve body than end sections of a proximal side slit of the valve body, and the protrusion section having a curved proximal-facing surface;

the annular member possessing a distal-facing surface facing towards the hub, the through-hole in the annular member narrowing in size in a direction toward the distal-facing surface of the annular member, and wherein a thickness of the protrusion section between the distal-facing surface and the curved proximal-facing surface decreases toward a central axis of the through-hole; and wherein the distal-facing surface includes a concave section that is recessed toward a proximal direction, the concave section being positioned radially between the protrusion section and an annular flat surface of the distal-facing surface of the annular member that is in direct contact with the proximal-facing surface of the valve body.

2. The introducer sheath according to claim 1, wherein the protrusion section protrudes from an inner circumferential edge section surrounding the through-hole in the annular member.

3. The introducer sheath according to claim 1, wherein a wall surface of the through-hole decreases in diameter from the proximal side toward a distal side, and wherein the wall surface is a curved surface that curves in a direction from the proximal side toward the distal side.

4. The introducer sheath according to claim 3, wherein the wall surface of the through-hole in the annular member possesses a radial direction width on a projection plane viewed from proximal side that is equal to or larger than a radial direction width of a portion of the annular member that is radially outside the wall surface of the through-hole on the projection plane.

5. The introducer sheath according to claim 1, wherein an entire surface of the annular member facing proximally is curved.

6. The introducer sheath according to claim 5, wherein a cross section of the curved surface along a direction from the proximal side toward the distal side is a curved line defined by one of a parabola, a quadratic function, an exponential function, and a logarithmic function.

7. The introducer sheath according to claim 6, wherein an inclination angle of a tangent of the curve with respect to a surface that is orthogonal to the central axis of the through-hole at a distal end section of the through-hole constitutes a distal side angle, and an inclination angle of the curve with respect to the surface that is orthogonal to the central axis of the through-hole at a proximal end section of the through-hole constitutes a proximal side angle, the distal side angle being larger than proximal side angle.

8. The introducer sheath according to claim 7, wherein the inclination angle of the curve continuously changes from the proximal side angle to the distal side angle.

9. The introducer sheath according to claim 1, wherein an inner diameter of a distal side terminal end of the protrusion section of the annular member is smaller than an inner diameter of the hub, and the protrusion section reaches a position further on the central side than the inner diameter of the hub.

10. The introducer sheath according to claim 1, wherein at least one of the annular member and the hub includes a flat surface section that has a flat surface, which contacts the valve body.

11. An introducer sheath comprising:
a tubular member that includes a hollow section through which an elongated body is freely insertable;
a hub that includes an inner space which communicates with the hollow section of the tubular member and is provided on a proximal side of the tubular member;
a valve body positioned in the inner space of the hub, the valve body possessing a proximal-facing surface facing away from the tubular member and a distal-facing surface facing toward the tubular member, the valve body including a slit that communicates with the distal-facing surface of the valve body;
an annular member that contacts the valve body to fix the valve body in the inner space, the annular member including a through-hole into which the elongated body is insertable, the annular member possessing a through-hole passing completely through the annular member, the slit in the valve body being exposed at the through-hole in the annular member to permit the elongated medical device to be inserted through the through-hole in the annular member and into the slit in the valve body;
the annular member including a protrusion section that protrudes toward the valve body so that a center of the valve body is pressed in a manner causing the valve body to be concave toward the distal side, the protrusion section contacting the valve body at a position further toward a central side of the valve body than end sections of a proximal side slit of the valve body, and the protrusion section having a curved proximal-facing surface;
the annular member possessing a distal-facing surface facing towards the hub, the through-hole in the annular member narrowing in size in a direction toward the distal-facing surface of the annular member, and wherein a thickness of the protrusion section between the distal-facing surface and the curved proximal-facing surface decreases toward a central axis of the through-hole; and
wherein the distal-facing surface includes a concave section that is recessed toward a proximal direction, the concave section being positioned radially between the protrusion section and an annular flat surface of the distal-facing surface of the annular member that is in direct contact with the proximal-facing surface of the valve body.

12. The introducer sheath according to claim 11, wherein the protrusion section protrudes from an inner circumferential edge section surrounding the through-hole in the annular member.

13. The introducer sheath according to claim 1, wherein a wall surface of the through-hole decreases in diameter from the proximal side toward a distal side, and wherein the wall surface is a curved surface that curves in a direction from the proximal side toward the distal side.

14. An introducer sheath into which an elongated medical device is insertable, the introducer sheath comprising:

a sheath tube through which extends a lumen that is configured to receive the elongated medical device, the sheath tube possessing a proximal end;

a hub fixed to the sheath tube and positioned at the proximal end of the sheath tube, the hub possessing a through-hole extending throughout the hub and communicating with the lumen in the sheath tube, the hub possessing a recessed proximal end;

a valve body positioned in the recessed proximal end of the hub and covering the through-hole in the hub in a liquid-tight manner, the valve body possessing a proximal-facing surface facing away from the sheath tube and a distal-facing surface facing toward the sheath tube, the valve body including a slit that communicates with the distal-facing surface of the valve body;

an annular member separate from the valve body, the annular member being mounted on the proximal end of the hub and in contact with the proximal-facing surface of the valve body, the annular member possessing a through-hole passing completely through the annular member, the slit in the valve body being exposed at the through-hole in the annular member to permit the elongated medical device to be inserted through the through-hole in the annular member and into the slit in the valve body;

the annular member including a protrusion section that protrudes toward the valve body so that a center of the valve body is pressed in a manner causing the valve body to be concave toward a distal side, the protrusion section contacting the valve body at a position further toward a central side of the valve body than end sections of a proximal side slit of the valve body, and the protrusion section having a curved proximal-facing surface; and wherein the annular member possesses a distal-facing surface facing towards the hub, the distal-facing surface including a concave section that is recessed toward a proximal direction, the concave section being positioned radially between the protrusion section and an annular surface of the distal-facing surface of the annular member that is in direct contact with the proximal-facing surface of the valve body.

15. The introducer sheath according to claim 14, wherein the through-hole in the annular member narrows in size in a direction toward the distal-facing surface of the annular member.

16. The introducer sheath according to claim 14, wherein a wall surface of the through-hole decreases in diameter from the proximal side toward a distal side, and wherein the wall surface is a curved surface that curves in a direction from the proximal side toward the distal side.

17. The introducer sheath according to claim 16, wherein the wall surface of the through-hole in the annular member possesses a radial direction width on a projection plane viewed from proximal side that is equal to or larger than a radial direction width of a portion of the annular member that is radially outside the wall surface of the through-hole on the projection plane.

18. The introducer sheath according to claim 14, wherein an entire surface of the annular member facing proximally is curved, and wherein a cross section of the curved surface along a direction from the proximal side toward the distal side is a curved line defined by one of a parabola, a quadratic function, an exponential function, and a logarithmic function.

* * * * *